US012186093B2

(12) United States Patent
Salkola

(10) Patent No.: US 12,186,093 B2
(45) Date of Patent: Jan. 7, 2025

(54) METHOD AND SYSTEM FOR DETERMINING TOUCH SENSITIVITY THRESHOLD

(71) Applicant: ICARE FINLAND OY, Vantaa (FI)

(72) Inventor: Mika Salkola, Espoo (FI)

(73) Assignee: ICARE FINLAND OY, Vantaa (FI)

( * ) Notice: Subject to any disclaimer, the term of this patent is extended or adjusted under 35 U.S.C. 154(b) by 829 days.

(21) Appl. No.: 16/973,207

(22) PCT Filed: Jun. 3, 2019

(86) PCT No.: PCT/FI2019/050421
§ 371 (c)(1),
(2) Date: Dec. 8, 2020

(87) PCT Pub. No.: WO2019/234292
PCT Pub. Date: Dec. 12, 2019

(65) Prior Publication Data
US 2021/0251569 A1    Aug. 19, 2021

(30) Foreign Application Priority Data
Jun. 8, 2018 (FI) .................................... 20185528

(51) Int. Cl.
*A61B 5/00* (2006.01)
*A61B 3/16* (2006.01)

(52) U.S. Cl.
CPC .......... *A61B 5/4827* (2013.01); *A61B 5/0053* (2013.01); *A61B 5/4041* (2013.01); *A61B 5/6821* (2013.01); *A61B 3/16* (2013.01)

(58) Field of Classification Search
CPC ... A61B 5/4824; A61B 5/4827; A61B 5/0053; A61B 5/4041; A61B 5/4029;
(Continued)

(56) References Cited

U.S. PATENT DOCUMENTS 2,656,715 A * 10/1953 Tolman .................... A61B 3/16
33/832
5,433,211 A *  7/1995 Brammer ............. A61B 5/4827
600/552
(Continued)

FOREIGN PATENT DOCUMENTS

CA          789799 A      7/1968
CH          625408 A5     9/1981
(Continued)

OTHER PUBLICATIONS

Machine Translation of KR 101153348, Patent Translate, pp. 1-9, printed on May 7, 2024 (Year: 2012).*
(Continued)

*Primary Examiner* — Yi-Shan Yang
*Assistant Examiner* — Om Patel
(74) *Attorney, Agent, or Firm* — Ziegler IP Law Group LLC.

(57) ABSTRACT

A method of determining touch sensitivity threshold at a region of body of a human using a probe. The method includes setting first value for impact attribute of probe; releasing the probe towards the region, to impact the region with the first value for impact attribute; receiving first feedback from human in response to the impact of the probe with the first value for the impact attribute. The method further includes changing the first value of the impact attribute to set a second value; releasing the probe towards the region, to impact the region with the second value for the impact attribute; receiving a second feedback corresponding to the second value for the impact attribute. The method includes changing value of impact attribute until determination of touch sensitivity threshold as either a lowest value of sensing or a highest value of senselessness of probe based on the feedback.

11 Claims, 7 Drawing Sheets

(58) Field of Classification Search
CPC ... A61B 5/4035; A61B 5/4058; A61B 5/4064; A61B 5/407; A61B 5/4076; A61B 5/6821–6829; A61B 3/16; A61B 3/18; A61B 3/185

See application file for complete search history.

(56) References Cited

U.S. PATENT DOCUMENTS

| | | | | |
|---|---|---|---|---|
| 9,155,467 | B1 | * | 10/2015 | Enikov ............ A61B 3/16 |
| 2002/0049428 | A1 | * | 4/2002 | Bruce ............ A61F 9/008 606/4 |
| 2006/0178596 | A1 | | 8/2006 | Robichaud et al. |
| 2011/0082384 | A1 | | 4/2011 | Harte et al. |
| 2012/0220892 | A1 | | 8/2012 | Gandhi et al. |

FOREIGN PATENT DOCUMENTS

| | | | |
|---|---|---|---|
| CN | 101026997 | A | 8/2007 |
| CN | 101182578 | A | 5/2008 |
| CN | 101267787 | A | 9/2008 |
| CN | 106999047 | A | 8/2017 |
| EP | 3130281 | A2 | 2/2017 |
| JP | 2004528146 | A * | 9/2004 |
| JP | 2005529670 | A | 10/2005 |
| JP | 2017029715 | A | 2/2017 |
| JP | 2019502451 | A | 1/2019 |
| KR | 101153348 | * | 6/2012 |
| WO | WO-02091902 | A2 * | 11/2002 ............ A61B 3/16 |
| WO | 03105680 | A1 | 12/2003 |
| WO | WO-2012106593 | A2 * | 8/2012 ........ A61B 5/4041 |
| WO | WO-2016131055 | A1 * | 8/2016 |
| WO | 2017103330 | A1 | 6/2017 |
| WO | 2018014870 | A1 | 1/2018 |

OTHER PUBLICATIONS

Machine Translation of JP 2004528146 A, Patent Translate, pp. 1-15, printed on May 24, 2024 (Year: 2004).*

Japan Patent Office, Notice of Reasons for Refusal, Application No. 2020-567497, Mailed Mar. 2, 2023, 2 pages, English translation, 2 pages.

Finnish Patent and Registration Office, Search Report, Application No. 20185528, Mailed Jan. 7, 2019, 1 page.

PCT, Notification of Transmittal of The International Preliminary Report on Patentability, Application No. PCT/FI2019/050421, Mailed Jul. 8, 2020, 17 pages.

PCT, Notification of Transmittal of The International Search Report and The Written Opinion of The International Searching Authority, or the Declaration, Application No. PCT/FI2019/050421, Mailed Aug. 26, 2019, 15 pages.

China National Intellectual Property Administration, First Office Action and Search Report, Application No. 201980036633.9, Dated Nov. 17, 2023, 11 pages.

State Intellectual Property Office, First review opinion notice, Application No. 201980036633.9, Dated Nov. 17, 2023, 13 pages.

* cited by examiner

METHOD AND SYSTEM FOR DETERMINING TOUCH SENSITIVITY THRESHOLD

TECHNICAL FIELD

The present disclosure relates generally to touch sensitivity; and more specifically to systems for determining a touch sensitivity threshold at a region of body of a human, using the aforementioned method.

BACKGROUND

Skin is the largest organ in the body. Apart from functioning as a homeostatic, physiological, immunologic barrier for the body, the skin also functions as a complex sensory organ. The skin perceives surrounding objects and environmental factors, and constantly updates brain about such encounters. Such relay of messages is conducted by millions of sensory nerve receptors the skin is equipped with. In this process, the sensory nerve receptors send message to the brain and evoke touch sensitivity corresponding to the perceived sensation or physical stimulus. The touch sensitivity of an individual can be used to diagnose several different medical conditions. Specifically, such medical conditions are often associated with peripheral neural system (namely, peripheral neuropathy).

The touch sensitivity varies from person to person, however, a standard normal range persists for every normal person. Deviations from such normal range indicates hyposensitivity or hypersensitivity in an individual. Conventionally, physicians perform a physical examination employing application of articles, such as a needle, tuning fork, Semmes-Weinstein monofilament (SWF) and such like, to a specific body part (such as foot, arm, palm, eyes and so forth) to determine touch sensitivity in that part of the body of the person. Such quantitative methods require simultaneous questioning the person for any feeling of pain or pressure to detect potential peripheral neuropathy at the application site. The application site is considered to be insensate if the person fails to sense any pain and/or pressure even after increasing the impact of such articles. However, quantitative methods vary in effectiveness and provide inconsistent results (such as influenced by true positives, false positives, true negatives, and false negatives) corresponding to touch sensitivity. Furthermore, the conventional techniques fail to measure and derive a generic (for example, SI unit based) value to indicate a touch sensitivity threshold of a patient. Subsequently, making it difficult to determine a reference point between two patients at different measurement opportunities to follow a medical condition.

Recently, nerve conduction study (NCS) has garnered appreciation for its diagnosing ability to determine touch sensitivity in patients. The nerve conduction study (NCS) is an objective and standard technique capable of measuring quantitative neurophysiologic changes. However, the clinical uses of nerve conduction study (NCS) is limited due to limited availability and high cost involved in obtaining an electromyography equipment and supplies, thus making the procedure impractical for both the patient as well as the physicians.

Most recently, instruments, such as rebound tonometers (RT) Goldmann applanation tonometry (GAT), and so forth, are being used for measuring an intraocular pressure of an eye on the application site. Notably, eyes are most sensitive organs, with cornea of the eyes innervated by dense sensory nerves (namely, small-fibre nociceptives) that are capable of sensing painful stimuli. Such instruments calculate the intraocular pressure corresponding to external force experienced by the cornea of the eye.

It is important to derive a touch sensitivity of a cornea of an eye. Indeed, a touch sensitivity of the cornea is important for overall physiological functioning of the eye. The touch sensitivity of the cornea can change due to different reasons. As an example, several systemic or eye-related diseases can decrease touch sensitivity e.g. diabetic neuropathy, herpes, rheumatism. Decreased touch sensitivity is a potential reason for dry eye syndrome and it increases significantly the risk for prolonged eye infections. The changes in the level of the touch sensitivity can indicate some of the mentioned and several other diseases or anomalies in overall physiological conditions in eyes.

Contact lenses are widely used. Monitoring corneal touch sensitivity threshold value (CTT) is important for all the contact lens users. Hypersensitivity of cornea causes discomfort when wearing contact lenses. Decreased touch sensitivity should be an exclusion criterion for using contact lenses because of the decreased sensory capability to recognize the early stages of potential eye infections.

In addition, invasive eye operations through cornea such as refractive and cataract surgery have an effect on corneal sensory nerves and thus to the touch sensitivity of the cornea. Therefore, monitoring corneal touch sensitivity threshold before and after invasive eye operations is an important method to evaluate the loss of sensory nerves during the operation and to follow the recovery process.

Document US 2006/178596 presents a sensory testing system and a method of using a sensory testing system to determine sensory pressure thresholds as well as a method of diagnosing a condition characterized by impaired neural function by using a sensory testing system to determine sensory pressure thresholds. Document WO 2012/106593 discusses a system for assessing peripheral nerve damage in a subject. The system includes a pressure application device and a computer. The system applies pressure to a selected body part of a subject in a desired pattern and continues the application of pressure until a pain threshold for the subject is achieved. Document US 2011/082384 discloses a computer-controlled sensory testing system that can be used to further pain research and aid in the clinical diagnosis and treatment of pain syndromes. The system includes actuators to deliver pressure/deformation (strain), auditory, olfactory, and other stimuli to a subject. The system includes software to control the delivery of the stimuli. The system is further operable to receive feedback regarding the stimuli received.

Therefore, in light of the foregoing discussion, there exists a need to overcome the aforementioned drawbacks associated with determining touch sensitivity threshold.

SUMMARY

The present disclosure seeks to provide a method of determining a touch sensitivity threshold at a region of body of a human using a probe. The present disclosure also seeks to provide a system for determining a touch sensitivity threshold at a region of body of a human, using the aforementioned method. The present disclosure seeks to provide a solution to the existing problems of measurement inaccuracies and inefficiency in deriving a generic value corresponding to touch sensitivity. An aim of the present disclosure is to provide a solution that overcomes at least partially the problems encountered in prior art and provides an accurate method and system for determining a touch sensitivity threshold at a region of body of a human.

In one aspect, an embodiment of the present disclosure provides a method of determining a touch sensitivity threshold at a region of body of a human using a probe, the method comprising:
- (a) setting a first value for an impact attribute of the probe;
- (b) releasing the probe towards the region of body, to impact the region of body with the first value for the impact attribute;
- (c) receiving a first feedback from the human in response to the impact of the probe with the first value for the impact attribute at the region of body;
- (d) changing, by increasing or decreasing the first value of the impact attribute to set a second value for the impact attribute of the probe;
- (e) releasing the probe towards the region of body, to impact the region of body with the second value for the impact attribute;
- (f) receiving a second feedback from the human in response to the impact of the probe with the second value for the impact attribute at the region of body; and
- (g) repeating steps (d) to (f) until the touch sensitivity threshold is determined as either:
  - a lowest value of sensing of the probe based on the feedback; or
  - a highest value of senselessness of the probe based on the feedback,
  wherein the feedback corresponds to sensing of the probe or senselessness of the probe.

In another aspect, an embodiment of the present disclosure provides a system for determining a touch sensitivity threshold at a region of body of a human, the system comprising:
a housing comprising:
  - a probe detachably arranged within the housing, wherein the probe is operable to impact the region of body with a predefined impact attribute;
  - a probe attachment means operable to retain the probe within the housing; and
  - a probe release means operable to release the probe towards the region of body, the probe release means being a driver coil,
  wherein an induction coil of the probe release means is operable to produce a magnetic force to actuate the probe:
    in a first direction to release the probe from the housing; or
    in a second direction to retract the probe into the housing;
a feedback means to receive feedback from the human after the impact of the probe with the region of body; and
a controller operatively coupled to the probe attachment means, the probe release means and the feedback means, wherein the controller is operable to:
  - (a) setting a first value for an impact attribute of the probe;
  - (b) releasing the probe towards the region of body, to impact the region of body with the first value for the impact attribute;
  - (c) receiving a first feedback from the human in response to the impact of the probe with the first value for the impact attribute at the region of body;
  - (d) changing, by increasing or decreasing the first value of the impact attribute to set a second value for the impact attribute of the probe;
  - (e) releasing the probe towards the region of body, to impact the region of body with the second value for the impact attribute;
  - (f) receiving a second feedback from the human in response to the impact of the probe with the second value for the impact attribute at the region of body; and
  - (g) repeating steps (d) to (f) until the touch sensitivity threshold is determined as either:
    - a lowest value of sensing of the probe based on the feedback; or
    - a highest value of senselessness of the probe based on the feedback,
    wherein the feedback corresponds to sensing of the probe or senselessness of the probe.

Embodiments of the present disclosure substantially eliminate or at least partially address the aforementioned problems in the prior art and enables accurate measurement of touch sensitivity threshold at a region of body of a human in a patient/user-friendly manner.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
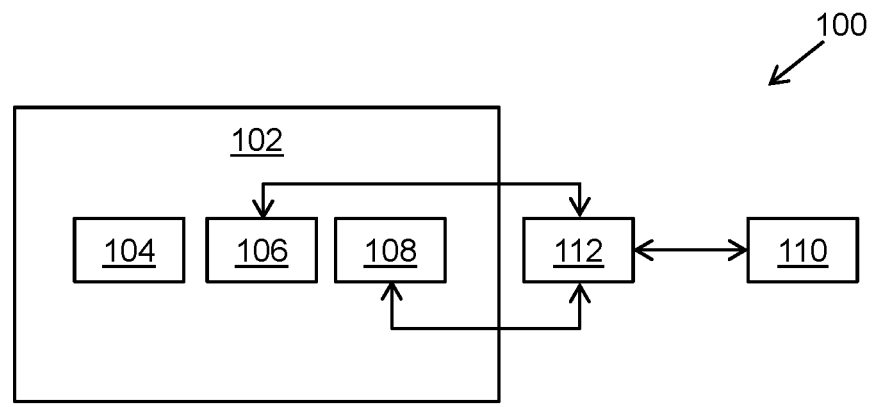
FIGS. 1 and 2 are block diagrams of a system for determining a touch sensitivity threshold at a region of body of a human, in accordance with various embodiments of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method of determining a touch sensitivity threshold at a region of body of a human using a probe, the method comprising:
- (a) setting a first value for an impact attribute of the probe;
- (b) releasing the probe towards the region of body, to impact the region of body with the first value for the impact attribute;
- (c) receiving a first feedback from the human in response to the impact of the probe with the first value for the impact attribute at the region of body;
- (d) changing, by increasing or decreasing the first value of the impact attribute to set a second value for the impact attribute of the probe;
- (e) releasing the probe towards the region of body, to impact the region of body with the second value for the impact attribute;
- (f) receiving a second feedback from the human in response to the impact of the probe with the second value for the impact attribute at the region of body; and
- (g) repeating steps (d) to (f) until the touch sensitivity threshold is determined as either:
  - a lowest value of sensing of the probe based on the feedback; or
  - a highest value of senselessness of the probe based on the feedback, wherein the feedback corresponds to sensing of the probe or senselessness of the probe.

In another aspect, an embodiment of the present disclosure provides a system for determining a touch sensitivity threshold at a region of body of a human, the system comprising:
- a housing comprising:
  - a probe detachably arranged within the housing, wherein the probe is operable to impact the region of body with a predefined impact attribute;
  - a probe attachment means operable to retain the probe within the housing; and
  - a probe release means operable to release the probe towards the region of body, the probe release means being a driver coil, wherein an induction coil of the probe release means is operable to produce a magnetic force to actuate the probe:
    - in a first direction to release the probe from the housing; or
    - in a second direction to retract the probe into the housing
- a feedback means to receive feedback from the human after the impact of the probe with the region of body; and
- a controller operatively coupled to the probe attachment means, the probe release means and the feedback means, wherein the controller is operable to:
  - (a) setting a first value for an impact attribute of the probe;
  - (b) releasing the probe towards the region of body, to impact the region of body with the first value for the impact attribute;
  - (c) receiving a first feedback from the human in response to the impact of the probe with the first value for the impact attribute at the region of body;
  - (d) changing, by increasing or decreasing the first value of the impact attribute to set a second value for the impact attribute of the probe;
  - (e) releasing the probe towards the region of body, to impact the region of body with the second value for the impact attribute;
  - (f) receiving a second feedback from the human in response to the impact of the probe with the second value for the impact attribute at the region of body; and
  - (g) repeating steps (d) to (f) until the touch sensitivity threshold is determined as either:
    - a lowest value of sensing of the probe based on the feedback; or
    - a highest value of senselessness of the probe based on the feedback,
  - wherein the feedback corresponds to sensing of the probe or senselessness of the probe.

The present disclosure provides the aforementioned method and the aforementioned system for determining the touch sensitivity threshold at the region of body of the human, via such a method. Beneficially, the aforementioned method is simple and requires lesser computational efforts for receiving, storing and displaying the derived measurement results in generic values. Consequently, additionally, the generic value may be used to determine reference point between two different participants (or two patients, or a patient and a normal human) and following-up with an associated medical condition. Additionally, the aforementioned system is light weight and simple to operate in both horizontal as well as inclined directions in a more secure way. Beneficially, the system may be used at any part of the body, cornea or skin, such as leg, hand, feet, and so forth, to provide substantially-constant measurements through a series of measurements associated with the touch sensitivity threshold at the region of body. Furthermore, the measurements are rapid and do not require any specially-trained operators or anaesthetizing the participant. Therefore, the system is cost-efficient and operable in a user/patient-friendly manner.

Throughout the present disclosure, the term "human" used herein refers to an individual, a group of individuals, a patient, and so forth. Furthermore, the human may be receiving or registered to receive medical services in a specific domain, such as medicine, neurology, and such like. Furthermore, it may be beneficial to acquire such services from an expert in a domain required by the human. Moreover, the experts are required to evaluate the human, for example, a neurologist may determine neural activities of an individual, who is suffering from or is on the verge of developing a neural disorder such as a diabetic peripheral neuropathy.

Throughout the present disclosure, the term "region of body" used herein refers to different body parts of the human. Specifically, the region of body associated with the peripheral nervous system (PNS) includes skin or cornea of the eyes that are innervated by millions of sensory neurons.

It is to be understood that peripheral neuropathy is a disorder of peripheral neural system, comprising autonomic nerves, motor nerves and sensory nerves. The peripheral nervous system (PNS) is responsible for sending messages from central nervous system (CNS), comprising brain and spinal cord, to one or more region of body of the human. In an example, the peripheral nervous system (PNS) is responsible for coordination of the brain and the body in an event of sensation or physical stimulus. Sensation or physical stimulus, for example, such as hot and cold, tingling, pain, twitching, cramps, lancinating, stabbing, pricking, burning, throbbing, aching, prickling, numbness, loss of co-ordination, proprioception and weakness in various regions of body are associated with peripheral neuropathy. Often the peripheral neuropathy is associated with an underlying medical condition, such as diabetic neuropathy, muscle paralysis, Bell's palsy, and the like. Notably, people suffering from such neuropathies lack in the ability to perceive pain and/or pressure and lose touch sensitivity.

Throughout the present disclosure, the term "touch sensitivity" used herein refers to one of the five senses along with taste, smell, hearing and seeing. Specifically, touch sensitivity refers to the ability to encounter proximity of an external object or force of such object on a touch surface. More specifically, an individual perceives touch sensitivity when they hold, caress, operate, feel or otherwise encounter something with an application area at any region of body, such as skin (of leg, hand, feet), cornea of the eye and so forth. Furthermore, the touch sensitivity stimulates sensory receptors in the region of body that is subjected to aforementioned sensation or physical stimulus. The sensory receptors conduct nerve impulse to brain, which interprets such stimuli and make them identifiable or perceived by the affected region of body of the human.

It will be appreciated that as a sensory organ of the body, the skin is adapted to haptic perceptions, tactile sensations and proprioception; and a fine network of millions of sensory nerve receptors constantly updates brain about the perception of surrounding objects and environmental factors. Each of the different types of sensory nerve receptors, such as mechanoreceptors, thermos-receptors, chemoreceptors, nociceptors, and so forth, pick up a specific type of touch. For example, mechanoreceptors are responsive to any kind of mechanical deformation, thermos-receptors differentiate between hot and cold, chemoreceptors sense chemicals produced within the skin and nociceptors detect painful stimuli. The sensory nerve receptors conduct the message corresponding to different types of touch to neurons along a specific pathway. For example, pain has its own pathway, i.e. some receptors that sense pain and pass such specific type of touch to a neuron connected with several other neurons in a pathway. Similarly, temperature has its own pathway. However, all pathways lead to a common sensory organ, the brain, where the message is sent. Amongst all the sensory organs, eyes are the most sensitive organs. Specifically, cornea of the eye receives the densest sensory innervations of the body. More specifically, small-fibre nociceptive neurons innervate the cornea of the eyes and are responsible for sensing painful stimuli and conducting impulses through their sensory endings. The nociceptives are the primary afferent (sensory) nerve fibres that respond to pain associated with noxious mechanical (namely, painful pressure, cutting, squeezing, and such like) thermal (namely, burning or chilling), and chemical stimuli (such as chili powder in eye). Therefore, in a most preferred embodiment, the eye surface innervated by small-fibre nociceptives is a potential organ to measure the sensitivity of the human.

It will also be appreciated that the sensory nerve receptors can sense a sensation or physical stimulus only if it is strong enough to stimulate the sensory nerve receptors. In other words, sensory nerve receptors can trigger a signal, to be passed along the neuron into the spinal cord, only when the human is subjected to a noxious stimulus that induces pain and/or pressure. Furthermore, the pain and/or pressure are sensed once a certain threshold is achieved. Throughout the present disclosure, the term "threshold" used herein refers to a level, a point or value at or above which a physiological or psychological effect begins to be produced. In other words, an effect of stimuli is perceivable above a threshold, while it ceases to exist below the threshold. It will be appreciated that a degree of stimulation of a nerve produces a response upon reaching a threshold.

For example, if touch sensitivity threshold of an individual is approximately 2 kgm-1 s-2 (SI unit derived from pressure stimuli $p=m*a/A$; wherein p is pressure, m is mass of the probe, a is the acceleration of the probe, and A is the area of impact at the region in contact with the probe), and if a stimulus of 0.5 kgm-1 s-2 is applied on a region of body of the individual, the individual will not detect the stimulus because the stimulus of 0.5 kgm-1 s-2 is lower than the touch sensitivity threshold (2 kgm-1 s-2). If a stimulus of 4 kgm-1 s-2 is applied on the same region of body of the individual, the individual will detect the stimulus because the stimulus of 4 kgm-1 s-2 is greater than the touch sensitivity threshold (2 kgm-1 s-2). It may be noted that the touch sensitivity threshold varies from one individual to another, and optionally, changes accordingly with age or medical conditions, such as a stroke, a traumatic incident, or a similar persisting condition, associated with the individual.

Optionally, the touch sensitivity threshold is determined as at least one of: a numerical value, a grade on a predefined scale. For example, the touch sensitivity may be a feeling of pain, less pain, no pain, no sensitivity at all. And the touch sensitivity threshold as measured on a predefined scale of 1 to 10, where 1 indicates a feeling of 'no', 2 indicates a feeling of 'little pain', and so forth, while 10 indicates a feeling of 'intense pain'. Preferably, the touch sensitivity threshold is dependent on the impact of the probe at the region of body. Moreover, touch sensitivity threshold must be a lowest value of sensing the probe or a highest value of senselessness of the probe.

The system for determining a touch sensitivity threshold at a region of body of a human comprises the housing. Specifically, the housing refers to a hollow encasing component having an interior and exterior portion. More specifically, the housing has a front part, a rear part and a middle part.

Optionally, the housing has a tubular form-factor. The tubular form-factor of the housing provides a compact structure that is free from sharp edges. Moreover, such a design of the housing is simple and easy to fabricate. Another potential benefit of the tubular design is that it provides significantly more usable internal space for placing the components of the aforementioned system, with respect to the space it occupies, when compared to other forms.

Alternatively, the housing has elliptical or a cylindrical form-factor.

The housing comprises the probe detachably arranged within the housing, wherein the probe is operable to impact the region of body with the predefined impact attribute. Throughout the present disclosure, the term "probe" refers to a movable element, movement of which produces an input sensory signal at the region of body. The probe is configured to be launched towards the region of body and impact the region of body. The impact of the probe arouses sensory cells innervating the region of body to initiate a conduction of message to the brain and back. The conduction of message is iterated in the form of a feedback associated with the predefined impact attribute and provided by the human. According to an embodiment the probe is detachably arranged within the housing using an attachment means. An example of attachment means is an attachment coil or a magnet. The magnetic force is used to retain the probe in the housing.

Throughout the present disclosure, the term "impact attributes" used herein refers to a predefined parameter for launching the probe towards the region of body of the human and/or with which the probe impacts the region of body. Optionally, the impact attribute of the probe comprises at least one of: speed, acceleration, kinetic energy, kinetic energy per unit area of impact, momentum, momentum per unit area of impact, pressure induced by the impact, duration of the impact. For example, the impact attribute is expressed as speed or velocity (vector quantity referring to speed in a specific direction) 'v'. The probe is operable to be launched towards the human at a speed to cover a specific distance 'd' from an initial position to a final position, i.e. the surface of the region of body in a specific time period 't', such that $v=d/t$. As a note the term acceleration in the context of present disclosure refers to positive and negative acceleration (i.e to deceleration).

In another example, the impact attribute is expressed as kinetic energy 'KE'. The probe is operable to be launched towards the human at a kinetic energy, as a factor of the mass 'm' of the prove and acceleration required by the probe to attain a velocity 'v', such that $KE=½*(m*v^2)$. Alternatively, the impact attribute may be expressed in terms of the kinetic energy 'KE' per unit area of impact 'A' at the region of body in contact with the probe, such that impact of the probe is $KE/A$.

In yet another example, the impact attribute is expressed as momentum 'P' as a product of mass 'm' and velocity 'v' of the probe, such that $P=mv$.

In yet another example, the impact attribute may be expressed in terms of the momentum 'P' exerted per unit area of impact 'A' at the region of body in contact with the probe, such that impact of the probe is $P/A$.

In yet another example, the impact attribute is expressed as the change in velocity of the probe during its launch and during its rebound, namely acceleration or deceleration, such that $a=d/dt(v)$ or $\Sigma \int \Delta v/\Delta t$.

In yet another example, the impact attribute is expressed as pressure 'p' as a product of mass 'm', acceleration 'a' calculated per unit area of impact 'A', such that $p=m*a/A$.

In yet another example, the impact attribute is expressed as duration of impact.

In an exemplary implementation, impact attribute of the probe is determined based on the pressure exerted by the probe at the region of body as illustrated in Table 1. The probe with a mass m 2.5*10E−5 kg and an area of impact A of 2.5*10E−5 m2 is operable to travel a distance d of 5*10E−4 m from its initial position to the final position, i.e. the surface of the region of body. The probe is launched to impact the region of body and rebound from the surface. Subsequently, a change in acceleration of the probe, i.e. difference between the velocity of probe at the time of launch and at the time of its rebound is determined as: the impact attribute of the probe expressed as pressure 'p' that corresponds to be associated with touch sensitivity.

TABLE 1

| m (kg) | A (m2) | a (m/s2) | Δv (m/s) | Δt (s) | P (Pa) |
|---|---|---|---|---|---|
| 2.5E−5 | 1.96E−7 | 350 | 0.35 | 0.001 | 4.63E4 |

Alternatively, the impact attribute may be expressed in terms of the pressure 'p' exerted by a probe of mass 'm' per unit area of impact 'A' at the region of body in contact with the probe under an influence of gravity (such as, when the probe is held vertically or perpendicularly with respect to the surface of the region of body), such that $P=m*g/A$, wherein g is acceleration due to gravity (approximated to be 10 m/s^2).

Referring to Table 1, impact attribute of the probe is determined based on the pressure exerted by the probe at the region of body under the influence of gravity at the region of body as illustrated in Table 2. Subsequently, force F exerted by the probe at the surface of the region of body is determined as:

$F=m*a$, wherein $a=10$ m/s^2

In an embodiment, the region of body may be an eye surface. In another embodiment, the region is body may be skin, such as skin of leg, hand, and so forth. It will be appreciated that form-factors and weight of the probe will be different for the measurements conducted on the eye surface from that selected for the skin. Additionally, the distance between the probe and the surface of the region of body under consideration is also different for the eye and the skin. Specifically, first two first rows of the Table 2 depict measurement of pressure p at the eye surface and last row depicts measurement of pressure p at the skin as:

TABLE 2

| p = F/A | | | | |
|---|---|---|---|---|
| d (m) | m (kg) | A (m2) | F (N) | p (Pa) |
| 12E−5 | 11E−6 | 1.13E−8 | 1.1E−4 | 9.73E3 |
| 12E−5 | 200E−6 | 1.13E−8 | 2.0E−3 | 1.77E5 |
| 5E−4 | 1000E−6 | 1.96E−7 | 1.00E−1 | 5.09E5 |

It may be noted that the pressure p exerted by the probe is lesser for the eye surface as compared to the skin. Notation "E" in this description refers to exponent term i.e. for example 1E-2 is 0.01 (i.e ¹⁄₁₀₀).

It will be appreciated that launching a probe at the region of body is a function of the speed with which it is launched, the momentum achieved by the probe, the deceleration with which the probe rebounds, the mass of the probe, the form-factors of the probe, the area of impact of the probe with the region, and the pressure felt by the region upon hit by the probe. Therefore, different results are expected for probes with different form-factors and/or weights, even when a constant speed or acceleration is provided to the probe.

Optionally, the probe is associated with at least one of: a predetermined weight, a predefined form-factor. In other words, the probe may be of varying weights and form-factors corresponding to the sensitivity of region of body. Form-factor is an aspect of hardware design which defines and prescribes the size, shape, and other physical specifications of components of a system. Specifically, form-factors represent a broad class of similarly sized components or prescribe a specific standard. Notably, smaller form-factors offer more efficient use of limited space, greater flexibility in the placement of components within a larger assembly, reduced use of material, and greater ease of transportation and use. However, smaller form-factors typically incur greater costs in the design, manufacturing, and maintenance phases of the engineering lifecycle, and do not allow the same expansion options as larger form-factors. For example, notebook computers are a form-factor due to the same "clamshell" form in a typically rectangular shape and opening to a keyboard on the flat surface and a screen on the top. Notebook computers are further available in different form-factors, such as an ultra-book, a netbook, and a convertible tablet. Additionally, form-factors are adaptable. For example, a probe targeted at the eye surface may be lightweight, with a smaller form-factor and impact attributes as compared to the probe targeted at the skin of leg. Furthermore, the position of probe against the targeted region of body may vary depending on the placement of such region of body. For example, the rebound tonometer may be used in a position horizontal or at an inclination to the region of body. Additionally, the probe may be hollow or solid. Furthermore, the probe may be made of plastic, elastomeric or glass. Furthermore, the probe typically comprises at least some magnetic material. The magnetic material can comprise ferromagnetic material and/or paramagnetic material. The cross-section of the probe may be circular, tubular, cylindrical, square, hexagonal, elliptical, or any other shape suitable for exerting force on the region of body of the human. In a preferred embodiment, the probe has a circular cross-section to allow a friction-less movement of the probe from and back into the housing. Therefore, the position, shape, dimensions, material of the probe are not fixed and can be adapted depending upon each case.

Optionally, the probe may be replaceable to ensure hygienic measurement experience. More optionally, a new probe may be inserted in the space within the housing to ensure hygienic measurement experience. In an example, a new probe may be inserted in the space within the housing for each new session while determining the touch sensitivity or intraocular pressure of the cornea of the eye. It is appreciated that a same probe is typically not reused while measuring touch sensitivity at the eye surface for the same entity or for different entities. It is understood that eyes are the most sensitive organs of the body and are susceptible to catching infection or damage from the probes if not used in a hygienic and/or secure manner.

Optionally, the probe comprises a tip part and a body part. Furthermore, the probe may be of partly magnetic material, wherein the tip part is fabricated using a bio-compatible material and the body part is magnetic material. Such a tip part of the probe that is fabricated using bio-compatible material enables the probe to function in intimate contact with living tissue (for example, the cornea of the eye) of the human body without any negative effect, thereby ensuring the human's comfort and safety.

Optionally, the tip part of the probe is formed of a non-magnetic material, such as a plastic, elastomeric or glass material. The tip part can be made to be hard or soft or elastic or non-elastic. Optionally, at least a portion of the tip part of the probe comprises a probe heading area. At least a portion of the probe heading area comprises a flat or round surface and has a known area. It will be appreciated that the probe heading area is associated with an idea size. Specifically, the probe heading area with a smaller area exerts larger pressure during impact as compared to the probe heading area with a larger area.

Optionally, the probe is operable to move inside of the housing. The system is arranged such that the probe is initially at a position at least partly inside the housing. Alternatively, initially the probe may be completely inside the housing.

The housing comprises the probe attachment means operable to retain the probe within the housing. Optionally, the probe attachment means is an attachment coil. Furthermore, the attachment coil can be configured to be electrically controlled. Specifically, when the electric supply in the probe attachment means is turned ON, the attachment coil holds the probe in its initial position since a magnetic force is induced in the attachment coil. Therefore, regulating the current flowing in the attachment coil impacts the movement of probe in and out of the housing. Furthermore, regulating the current flowing in the attachment coil also prevents the probe from escaping from the housing, during measurements in horizontal as well as at an inclination with respect to the region of body. With measurement at an inclination is meant measurement in which the measurement is performed while the system is held or placed in such a position that the probe is moving in a direction forming an angle with respect to the horizontal plane during the measurements. Specifically, vertical measurement, wherein such angle is 90° (relative to horizontal plane), is to be considered as a special case of an inclined measurement, in which the measurements are performed with the system held or placed in a position that the probe moves vertically perpendicularly to the horizontal plane during the measurements. Alternatively, the probe attachment means comprises, but not limited to, a magnetic circuit, a mechanical lock, a frictional brake, and such like. The magnetic circuit located behind the rear part of the housing holds the probe securely once the probe is loaded into the housing. Optionally, the attachment means is or comprises a permanent magnet. In such optional embodiment the system preferably comprise also a release coil arranged to reduce/remove magnetic field force of the permanent magnet.

The housing comprises the probe release means operable to release the probe towards the region of body. The probe release means is a driver coil. The attachment coil of the probe release means is operable to produce a magnetic force in a first direction to release (or to actuate) the probe from the housing, or in a second direction to retract the probe into the housing.

Optionally, the probe release means is operable to actuate the probe by regulating a flow of current through the driver coil of the probe release means. Specifically, the current flown through the driver coil (the current induces a magnetic force), compensates (or cancels) the effect of the magnetic field of the probe attachment means and consequently produces a magnetic force in the probe release means that allows the probe to move in the first direction to release the probe from the housing or in the second direction to retract the probe into the housing. Furthermore, the current is flown into the driver coil from an external power supply. It is to be understood that the speed of the probe is controlled by the flow of current in the driver coil. Specifically, a higher current in the driver coil results in a higher speed with which the probe is released from the housing. Similarly, a lower current in the driver coil results in a lower speed with which the probe is released from the housing. Such an implementation of a probing system wherein the speed of the probe is controlled by the flow of current in the driver coil, facilitates rapid and accurate determination of touch sensitivity threshold at a region of a body of a human. It will be appreciated that the force applied by the probing system is critical for test accuracy and validity. Pursuant to the embodiments of the present disclosure, specific force levels can be applied to a region of body of a human, thereby facilitating an accurate assessment of the threshold touch sensitivity at the region of the body of the human.

Optionally, the probe is retracted back into the housing by introducing a current in the opposite direction to the driver coil.

According to an embodiment, the system comprises a probe measurement means. Furthermore, the probe measurement means comprises a measurement coil. The measurement coil is operable to measure the current resulting from the movement of the probe after the launch and the rebound of the probe respectively. The current is in practice induced by the probe movement since the probe comprises magnetic material.

Optionally, the driving coil and attachment coil can be physically a single coil arrangement. Optionally driving coil or attachment coil can be used as a measurement coil. Optionally the measurement coil can be used as driving coil or an attachment coil. Optionally the driving coil can be used as the attachment coil. Furthermore, in a mechanical construction of the system coils can be arranged is multiple ways with respect to each other. For example, the measurement coil can be closer to tip part than the driver coil or vice versa. In general, the driving coil, the release coil and the measurement coil are induction coils.

The housing further comprises the feedback means to receive feedback from the human after the impact of the probe with the region of body. Optionally, the feedback means is implemented as an input device, wherein the input device comprises at least one of a user interface, a keypad, an audio receiver for receiving tactile feedback or audio feedback. The user interface is operable to receive an input by way of buttons, joystick, slider to register (or log) the touch sensitivity corresponding to the impact of the probe, rendered on the user interface. Specifically, the input device may be used to register (or log) the touch sensitivity in terms of a "YES" or a "NO", a grade on a predefined scale. As mentioned above, the touch sensitivity threshold may be represented as for example, a feeling of pain, less pain, no pain, no sensitivity at all. Alternatively, the touch sensitivity threshold may be represented on a scale of 1 to 10, where 1 indicates a feeling of 'no', 2 indicates a feeling of 'little pain', and so forth, while 10 indicates a feeling of 'intense pain'. Further the input device (or feedback in general) might be used to collect from user if the user is a feeling of pain, less pain, no pain, no sensitivity at all or using said scale. Such an implementation of feedback means facilitates in ascertaining the touch sensitivity threshold in an accurate manner.

Optionally, the user interface of the feedback means comprises a display element configured to display the feedback input by the human. The display element relates to an optical component configured to allow display of at least a part of the feedback thereupon. In other words, a given display element is configured to receive feedback corresponding to a touch sensitivity thereupon. Optionally, the display element is substantially flat in shape. Alternatively, optionally, the display element is substantially curved in shape. Optionally, the display element is implemented for example by way of: Liquid Crystal Displays (LCD), Light Emitting Diode (LED)-based displays, Organic LED (OLED)-based displays, micro OLED-based displays and Liquid Crystal on Silicon (LCoS)-based displays.

The housing further comprises the controller operatively coupled to the probe attachment means, the probe release means and the feedback means. In operation, the controller regulates the actions of the probe attachment means, the probe release means and the feedback means The method of the present disclosure comprises setting a first value for the impact attribute of the probe. Furthermore, the controller is operable to set the first value for the impact attribute of the probe. Specifically, setting the first value for the impact attribute depends on the region of body of the human. More specifically, setting the first value for the impact attribute depends on the sensitivity of region of body of the human. For example, the region of body may be skin of a leg, and the first value for the impact attribute of the probe to impact the skin of a leg may be 0.1 N (i.e. $\frac{1}{10}$ N). In another example, the region of body may be skin of a hand, which is comparatively more sensitive as compared to the skin of the leg, consequently the first value for the impact attribute of the probe to impact the skin of a hand may be 0.07 N (i.e. $\frac{7}{100}$ N). In yet another example, the region of body may be an eye surface or the cornea, which is the most sensitive part of a human body, therefore the first value for the impact attribute of the probe to impact the eye surface or cornea may be 0.002 N. It is to be understood that a unit of measurement (i.e. Newton (N)) of the impact attribute does not intend to limit the scope of the disclosure.

The method further comprises releasing the probe towards the region of body, to impact the region of body with the first value for the impact attribute. Furthermore, the controller is operable to release the probe towards the region of body, to impact the region of body with the first value for the impact attribute. Specifically, the probe release means is operable to release the probe towards the region of body, wherein the probe release means comprises a driver coil. More specifically, the controller is operatively coupled to the probe release means and configures the probe release means to release the probe with the first value for the impact attribute towards the region of body of human.

It is understood that the probe released with the first value for the impact attribute towards the region of body is configured to hit the region of body and cause an impact of the probe with the first value for the impact attribute at the region of body. Consequently, the region of body senses the impact of the probe and retaliate in sensing or senselessness of the impact of the probe with the first value for the impact attribute.

The method further comprises receiving a first feedback from the human in response to the impact of the probe with the first value for the impact attribute at the region of body. Furthermore, the controller is operable to receive the first feedback from the human in response to the impact of the probe with the first value for the impact attribute at the region of body. Specifically, the feedback means is operable to receive feedback from the human after the impact of the probe with the region of body. More specifically, the controller is operatively coupled to the feedback means and configures the feedback means to receive feedback from the human after the impact of the probe with the region of body.

Throughout the present disclosure, the term "feedback" used herein refers to information about reaction to a situation, product, stimuli, and so forth. Specifically, the feedback allows modification or control of a process or system by its results or effects. More specifically, the feedback is a process which allows outputs of an action to be routed back as inputs to modify the next action in a cause-and-effect loop. In an embodiment, the feedback may be an indication of a feeling of sense associated with the impact of the probe. In another embodiment, the feedback may be the intensity of the sensing, i.e. pain level or feeling level (such as no feeling, little bit of feeling, clear feeling, and so forth).

Furthermore, human is required to provide the first feedback in response to the impact of the probe with the first value for the impact attribute at the region of body. Specifically, the human is required to provide feedback using the user interface of the feedback means. In other words, the system iterates the impact attribute of the probe towards the region of body of the human and collects feedback information using a feedback means.

The method further comprises changing, by increasing or decreasing the first value of the impact attribute to set a second value for the impact attribute of the probe. Specifically, the controller is operable to change, by increasing or decreasing the first value of the impact attribute to set a second value for the impact attribute of the probe. The change in the first value for the impact attribute corresponds to the touch sensitivity, i.e. whether induced by the first value for the impact attribute or not. In an instance, the first value for the impact attribute is increased to set a second value for the impact attribute until the second feedback corresponds to touch sensitivity at the region. Alternatively, the first value for the impact attribute is decreased to the second value for the impact attribute until the second feedback does not indicate touch sensitivity at the region. Optionally, the first value for the impact attribute and the second value for the impact attribute are determined as at least one of: a numerical value, a grade on a predefined scale.

Optionally, changing the first value for the impact attribute, by increasing or decreasing the first value for the impact attribute to obtain the second value for the impact attribute, comprises increasing or decreasing the value within: a predetermined step size; progressive step sizes; regressive step sizes; or using Newton-Raphson technique.

In an embodiment, a predetermined step size may be an ideal difference between one level and the next level. Step size is the increment or decrement to shift the values further to the next level. In an example, a step size of 2 would calculate a value for the predefined impact attribute every 2 units.

In another embodiment, the predetermined step size may be progressive step sizes, i.e. value of the next predefined impact attribute is increased with a constant step size; regressive step sizes, i.e. value of the next predefined impact attribute is decreased with a constant step size; or using Newton-Raphson technique.

In yet another embodiment, the Newton-Raphson technique may be employed to change the first value for the impact attribute to set a second value for the impact attribute of the probe. The Newton-Raphson technique is an iterative procedure that can be performed repeatedly to find a solution to an equation to a greater accuracy. Specifically, the iterative Newton-Raphson technique is employed when the first value for the impact attribute is increased to the second value for the impact attribute until the second value for the impact attribute induces touch sensitivity at the region, wherein the first value for the impact attribute fails to induce touch sensitivity at the region. In such scenario, a third impact attribute is selected as an average of the first value for the impact attribute and the second value for the impact attribute. Furthermore, if the third impact attribute fails to induce touch sensitivity at the region, then a fourth impact attribute is selected as an average of the second value for the impact attribute and the third impact attribute, considering that the touch sensitivity is induced at a level in between the second value for the impact attribute and the third impact attribute. However, if the third impact attribute induces touch sensitivity at the region, then the fourth impact attribute is selected as an average of the first value for the impact attribute and the third impact attribute, considering that the touch sensitivity is induced at a level in between the first value for the impact attribute and the third impact attribute. Similarly, the process may be iteratively performed to find a solution to an equation closest to a true value that is associated with touch sensitivity at the region.

Optionally, the first value for the impact attribute is changed using random step sizes. More optionally, the random step sizes increase or decrease. Beneficially, such correlation between impact of the probe and the touch sensitivity can be determined without hindsight of what is expected. Furthermore, smaller step size considers multiple data points for determining the desired result, and therefore yield an accurate touch sensitivity threshold of the region of body. Specifically, a lowest value of the impact attribute is selected to be the true value associated with touch sensitivity at the region. More optionally, the touch sensitivity threshold is selected as the lowest value of the impact attribute associated with touch sensitivity at the region.

More optionally, same force resulting from the launching probe may be repeated for multiple times, with different weights, form-factors and/or speed associated with the probe, to get a better correlation between force resulting from the launching probe and the touch sensitivity.

More optionally, repeating any of the above patterns multiple times or mixing the patterns may generate a better correlation between force resulting from the launching probe and the touch sensitivity. Alternatively, optionally, other iterative methods may be used to change the first value for the impact attribute.

The method further comprises releasing the probe towards the region of body, to impact the region of body with the second value for the impact attribute. Furthermore, the controller is operable to release the probe towards the region of body, to impact the region of body with the second value for the impact attribute. Specifically, the probe release means is operable to release the probe towards the region of body, wherein the probe release means comprises a driver coil. More specifically, the controller is operatively coupled to the probe release means and configures the probe release means to release the probe with the second value for the impact attribute towards the region of body of human.

It is to be understood that the second value for the impact attribute is selected due to failure of the first value for the impact attribute to generate sensitivity at the region of body. The probe released with the second value for the impact attribute towards the region of body is configured to hit the region of body and cause an impact of the probe with the second value for the impact attribute at the region of body. Consequently, the region of body senses the impact of the probe and retaliate in sensing or senselessness of the impact of the probe with the second value for the impact attribute.

The method further comprises receiving a second feedback from the human in response to the impact of the probe with the second value for the impact attribute at the region. Furthermore, the controller is operable to receive a second feedback from the human in response to the impact of the probe with the second value for the impact attribute at the region. The second feedback is iteratively received until touch sensitivity is perceived by the human in case senselessness was perceived when the region received an impact by the probe with the first value for the impact attribute. For example, if the first feedback indicates no sensitivity upon an impact by the probe corresponding to the first value for the impact attribute of the probe, (for example a force corresponding to static pressure/force of 0.1 N), in such case, a higher value for the impact attribute is selected and studied until a feedback of touch sensitivity is reported (or logged) associated with the higher value for the impact attribute with which the probe is launched. However, if the first feedback indicates a feeling of pain and/or pressure upon the impact by corresponding to the first value for the impact attribute of the probe, i.e. 10, in such case, a lower value for the impact attribute is selected and studied until a feedback of senselessness is reported (or logged) associated with the lower value for the impact attribute with which the probe is launched. Beneficially, the second value for the impact attribute is used to determine the touch sensitivity threshold at the region of body.

The method further comprises changing, by increasing or decreasing the first value of the impact attribute to set the second value for the impact attribute of the probe; releasing the probe towards the region of body, to impact the region of body with the second value for the impact attribute; receiving the second feedback from the human in response to the impact of the probe with the second value for the impact attribute at the region of body until touch sensitivity threshold is determined as a lowest value of sensing the probe based on the feedback, wherein the feedback corresponds to sensing of the probe. It is understood that the touch sensitivity threshold corresponds to the lowest value of the impact attribute at which the human perceives touch sensitivity. Therefore, the method disclosed in the present disclosure determines the touch sensitivity threshold after performing iterative measurements by varying the impact attributes of the probe.

Alternatively, the method comprises changing, by increasing or decreasing the first value of the impact attribute to set the second value for the impact attribute of the probe; releasing the probe towards the region of body, to impact the region of body with the second value for the impact attribute; receiving the second feedback from the human in response to the impact of the probe with the second value for the impact attribute at the region of body until determination of the touch sensitivity threshold as a highest value of senselessness of the probe based on the feedback, wherein the feedback corresponds to senselessness of the probe. It will be appreciated that the method employs use of probes with different weights, form-factors and impact attributes to determine the touch sensitivity threshold more accurately to the closest true value of touch sensitivity threshold for the human.

Optionally, the method comprises changing the value for the impact attribute by increasing until the feedback corresponds to sensing at the region of body. Specifically, the impact attribute of the probe is varied based on different patterns, wherein the pattern comprises any one of: a ramp-up, a ramp-down, iterative and random. The ramp-up pattern comprises setting a 'lower' first value for the impact attribute and impacting the region of body with a probe released with the first value for the impact attribute towards the region of body of the human. If the feedback associated with the first value for the impact attribute is not associated with touch sensitivity at the region of body, a 'higher' second value for the impact attribute is set. Optionally, the increase in first value for the impact attribute may be achieved using equal or random progressive step size, wherein each step size is equal or higher than the previous step size. Subsequently, the probe is released with the second value for the impact attribute towards the region of body of the human and the feedback associated with the second value for the impact attribute is obtained. The above step is repeated until a feedback corresponds to sensing at the region of body of the human.

Alternatively, optionally, the method comprises changing the value for the impact attribute by decreasing until the feedback corresponds to senselessness at the region of body. Specifically, the ramp-down pattern comprises setting a 'higher' first value for the impact attribute and impacting the region of body with a probe released with the first value for the impact attribute towards the region of body of the human. If the feedback associated with the first value for the impact attribute is associated with touch sensitivity at the region of body, a 'lower' second value for the impact attribute is set. Optionally, the decrease in first value for the impact attribute may be achieved using equal or random regressive step size. Subsequently, the probe is released with the second value for the impact attribute towards the region of body of the human and the feedback associated with the second value for the impact attribute is obtained. The above step is repeated until a feedback corresponds to senselessness at the region of body of the human.

Alternatively, optionally, the method comprises changing the value for the impact attribute by randomly varying until the feedback corresponds to one of sensing at the region of body or senselessness at the region of body. Specifically, the randomly varying the first value for the impact attribute to set a second value for the impact attribute comprises setting a random or pseudo-random value for the first value for the impact attribute with instruction to the human to provide feedback every time a touch sensing is felt. Depending on the feedback, the second value for the impact attribute is set and the feedback associated with the second value for the impact attribute is obtained. The above step is repeated until a feedback corresponds to touch sensitivity at the region of body of the human. Beneficially, such correlation between force resulting from the launching probe and the touch sensitivity can be determined without hindsight of what is expected.

Specifically, the controller is operable to change the value for the impact attribute by increasing until the feedback corresponds to sensing at the region of body; decreasing until the feedback corresponds to senselessness at the region of body; or randomly varying until the feedback.

Optionally, the system further comprises a server arrangement is communicatively coupled to the controller via a communication network. The server arrangement is a structure and/or module that includes programmable and/or non-programmable components configured to store to the touch sensitivity thresholds for a plurality of humans in a database. In an example, the communication network includes but not limited to, a cellular network, short-range radio (for example, such as Bluetooth®), Internet, a wireless local area network, and an Infrared Local Area Network, or any combination thereof.

Optionally, the method further comprises determining touch sensitivity threshold for each of a plurality of humans, by determining a reference touch sensitivity threshold using the touch sensitivity thresholds of the plurality of humans. The plurality of humans, randomly selected from a group of normal individuals who are not suffering from any medical condition, may be tested for determining touch sensitivity threshold for each of a plurality of humans. Specifically, the server arrangement is operable to determine touch sensitivity threshold for each of a plurality of humans. Furthermore, the server arrangement is operable to determine a reference touch sensitivity threshold using the touch sensitivity thresholds of the plurality of humans.

Optionally, the method further comprises storing the reference touch sensitivity threshold. Furthermore, optionally, the server arrangement comprises a database operable to store the touch sensitivity thresholds for a plurality of humans. Optionally, the reference touch sensitivity threshold, as well as the touch sensitivity threshold for each of a plurality of humans, may be stored as an absolute value based on a generic (International System of Units (SI) based) values. Alternatively, optionally, the reference touch sensitivity threshold and the touch sensitivity threshold for each of a plurality of humans may be stored as a grade on a predefined scale or as a range of values. Furthermore, the database relates to an organized body of digital information regardless of a manner in which the data or the organized body thereof is represented. More optionally, the database may be hardware, software, firmware and/or any combination thereof. For example, the organized body of digital information may be in a form of a table, a map, a grid, a packet, a datagram, a file, a document, a list or in any other form. The database includes any data storage software and system.

Optionally, the method further comprises determining a reference touch sensitivity threshold using the touch sensitivity thresholds of the plurality of humans. Specifically, by using touch sensitivity threshold for each of a plurality of humans a reference touch sensitivity threshold for a normal human, free from any medical condition, is determined. It is evident that the aforementioned system may be used to determine touch sensitivity threshold of a plurality of humans (humans or animals) to determine a normal level of touch sensitivity threshold in a normal entity. With normal entity is meant entity that is free of any medical condition that may increase or decrease touch sensitivity of the human. Therefore, a selection of normal entities is randomly made to determine the touch sensitivity threshold for each of the selected entities. Subsequently, an average absolute value for touch sensitivity threshold is calculated from all the touch sensitivity threshold of the selected entities. The average absolute value for touch sensitivity threshold is used as a reference point for the measurement of touch sensitivity threshold for the human with an underlying medical condition. Optionally, touch sensitivity at the region of body of the human may be monitored periodically, for example, one a month, to measure a difference in the sensing level of the human.

Optionally, the method comprises determining a difference between the touch sensitivity threshold of the human and the reference touch sensitivity threshold. In an instance, the difference between the touch sensitivity threshold of the human and the reference touch sensitivity threshold allows identification of potential patients associated with a medical condition such as hyposensitivity or hypersensitivity. Furthermore, the controller is operable to receive the reference touch sensitivity threshold from the server arrangement and determine a difference between the touch sensitivity threshold of the human and the reference touch sensitivity threshold. The controller may also be configured to correlate the difference between a touch sensitivity and a potential medical condition for the human. The controller may also be configured to correlate differences between a touch sensitivity and a potential medical condition for different humans. In an embodiment, the controller is operable to receive the previous measured, or in this scenario the reference touch sensitivity as measured in the previous month, from the server arrangement. The controller is further operable to determine the difference between the touch sensitivity threshold of the human for the current measurement and the reference touch sensitivity as measured in the previous month.

Optionally, the method further comprises correlating the difference with a potential medical condition for the human. Specifically, such reference touch sensitivity threshold may be used to identify individuals who are suffering from a medical condition or on the verge of developing a potential medical condition. Furthermore, the reference touch sensitivity threshold may be used to follow-up with certain medical condition and design treatment or interventions to control the condition within lower limits.

In an embodiment, if the touch sensitivity threshold of the human is higher than the reference touch sensitivity threshold, the human may be identified as being losing the ability to sense a physical stimulus or suffering from peripheral neuropathy. On the other hand, if the touch sensitivity threshold of the human is lower than the reference touch sensitivity threshold, then the human is identified as being hypersensitive towards a certain physical stimulus. Optionally, the reference touch sensitivity threshold may be represented as a range on a predefined scale. Specifically, the controller is further operable to correlate the difference between the touch sensitivity threshold of the human and the reference touch sensitivity threshold with a potential medical condition for the human. In an embodiment, the controller uses the current measurement and the reference touch sensitivity as measured in the previous month for a correlation of the difference of the two with a potential medical condition. Specifically, a reduced sensing level is an indication of various diseases, such as diabetes neuropathy, and so forth.

Optionally, the system comprises a separator part operatively coupled to the housing, wherein the separator part maintains a predefined separation between the housing (thus also probe before using the probe) and the region of body of the human. It is required that the probe is held at a predefined distance range from the surface of the region of body, such that the probe is launched with the predefined impact attribute towards the region of body of the human. It will be appreciated that the system is arranged such that initially the probe is held inside the housing, securely by a separator part. Upon inducing a magnetic field to propel the probe in the forward direction, the separator part is configured to allow the probe to impact the region. Specifically, the separator part is fabricated using a bio combatable material.

Optionally, the method further comprises determining an impact attribute of the probe associated with impact of the probe with the region of body. The probe launched with the first value for the impact attribute and/or the second value for the impact attribute towards the region of body hits the surface of the region with an impact force and returns from the region. During the rebound, the probe loses some of its predefined impact attribute to get decelerated.

Optionally, the probe measurement means is operable to determine an impact attribute of the probe associated with impact of the probe with the region of body. The probe measurement means comprises a measurement coil. Specifically, the impact attribute associated with impact of the probe bears a difference in value associated with the loss of energy during the launch of the probe and impact by the probe at the region of body. The impact attribute associated with impact of the probe is determined as at least one of: a numerical value, a grade on a predefined scale associated with the retraction of the probe back in the housing.

The probe release means may comprise an induction coil which is operable to produce a magnetic force to actuate the probe in a first direction to release the probe from the housing; or in a second direction to retract the probe into the housing. The driver coil is an induction coil.

Optionally, the same induction coil system as that of the probe attachment means and probe release means is operable to function as the probe measurement means for the aforementioned system. Specifically, the impact attribute associated with impact of the probe induces a voltage in the induction coil that is measured as the resultant of the impact of the probe.

In an exemplary implementation, once a threshold is established for the human, efficacy of drug or medical treatment may be studied and a medication or a treatment plan may be established respectively. Often, change in the threshold, corresponding to dosage and period of treatment, may be recorded at specified time points to analyse the effects of such dosage and period of treatment on the subject.

DESCRIPTION OF DRAWINGS

Referring to FIG. 1, illustrated is a block diagram of a system 100 for determining a touch sensitivity threshold at a region of body of a human, in accordance with an embodiment of the present disclosure. The system 100 comprises a housing 102, a feedback means 110 and a controller 112. The housing 102 comprises a probe 104, a probe attachment means 106 and a probe release means 108. The probe 104 is detachably arranged within the housing. The probe 104 is operable to impact the region with a predefined impact attribute. The probe attachment means 106 is operable to retain the probe within the housing. The probe release means 108 is operable to release the probe towards the region of body. The feedback means 110 is operable to receive feedback from the human after the impact of the probe with the region. The controller 112 is operatively coupled to the probe attachment means 106, the probe release means 108 and the feedback means 110.

Figure 2:
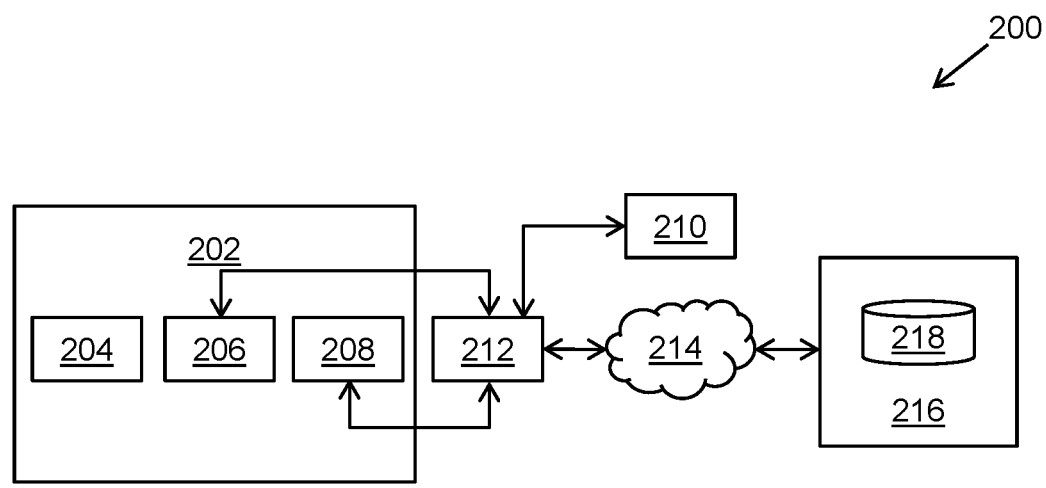

Referring to FIG. 2, illustrated is a block diagram of the system 200 for determining a touch sensitivity threshold at a region of body of a human, in accordance with another embodiment of the present disclosure. The system 200 comprises a housing 202, a feedback means 210 and a controller 212. The housing 202 comprises a probe 204, a probe attachment means 206 and a probe release means 208. The controller 212 is operatively coupled to the probe attachment means 206, the probe release means 208 and the feedback means 210. As shown, the system 200 further comprises a server arrangement 216 communicatively coupled to the controller 212 via a communication network 214. Furthermore, the server arrangement 216 comprises a database 218 operable to store the touch sensitivity thresholds for a plurality of humans.

Figure 3A:
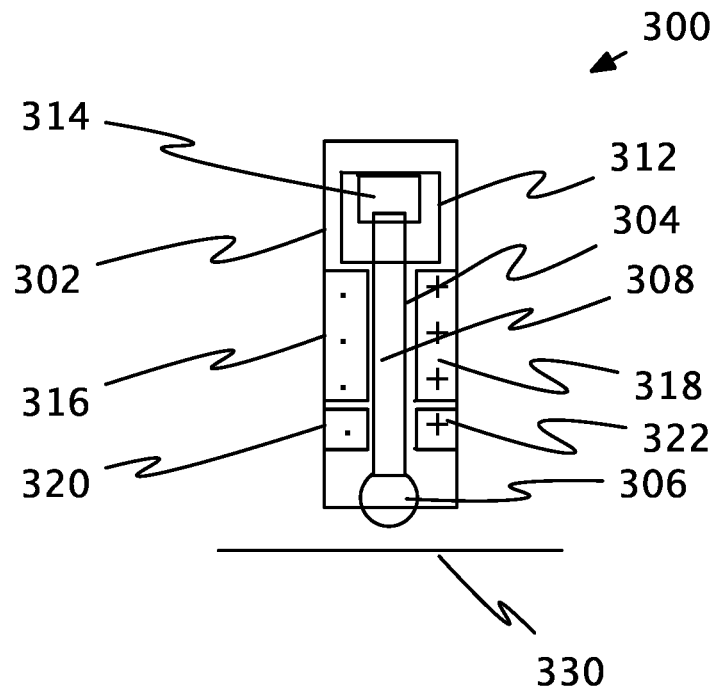
FIGS. 3A, 3B, 3C are schematic illustrations of a system for determining a touch sensitivity threshold at a region of body of a human, in accordance with various embodiments of the present disclosure.
Figure 3B:
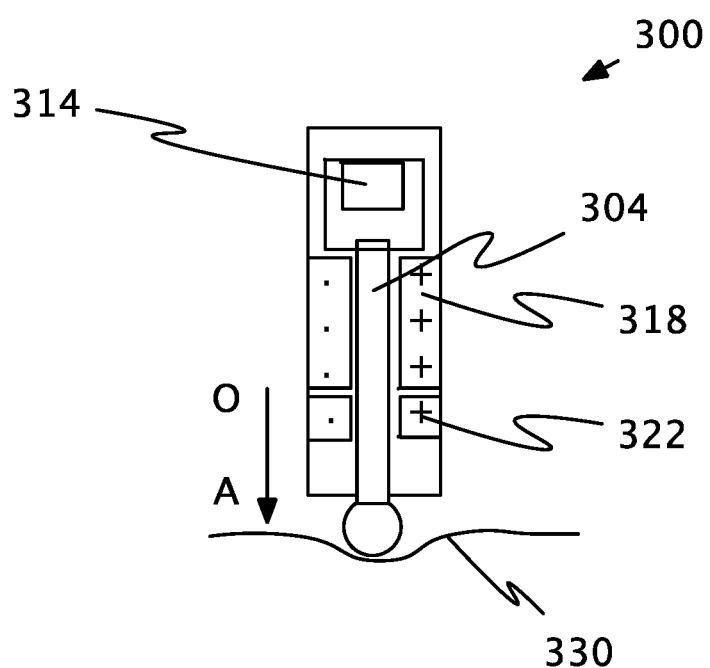
Figure 3C:
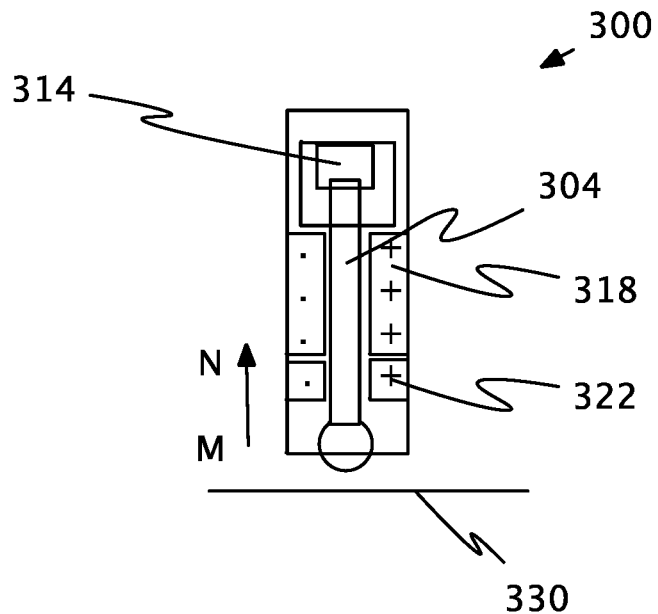
Figure 4:
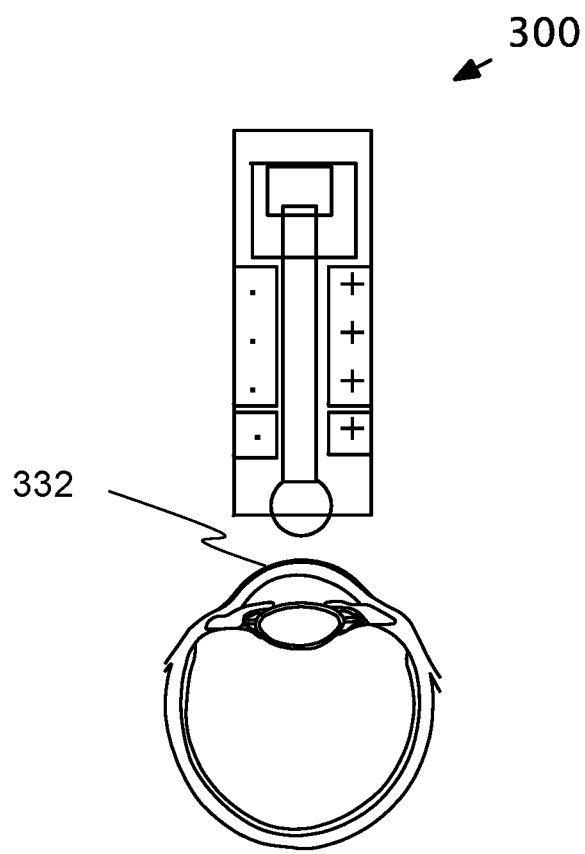
FIG. 4 is a schematic illustration of the system of FIGS. 3A, 3B, 3C in a utilized state, in accordance with an embodiment of the present disclosure.
Figure 5:
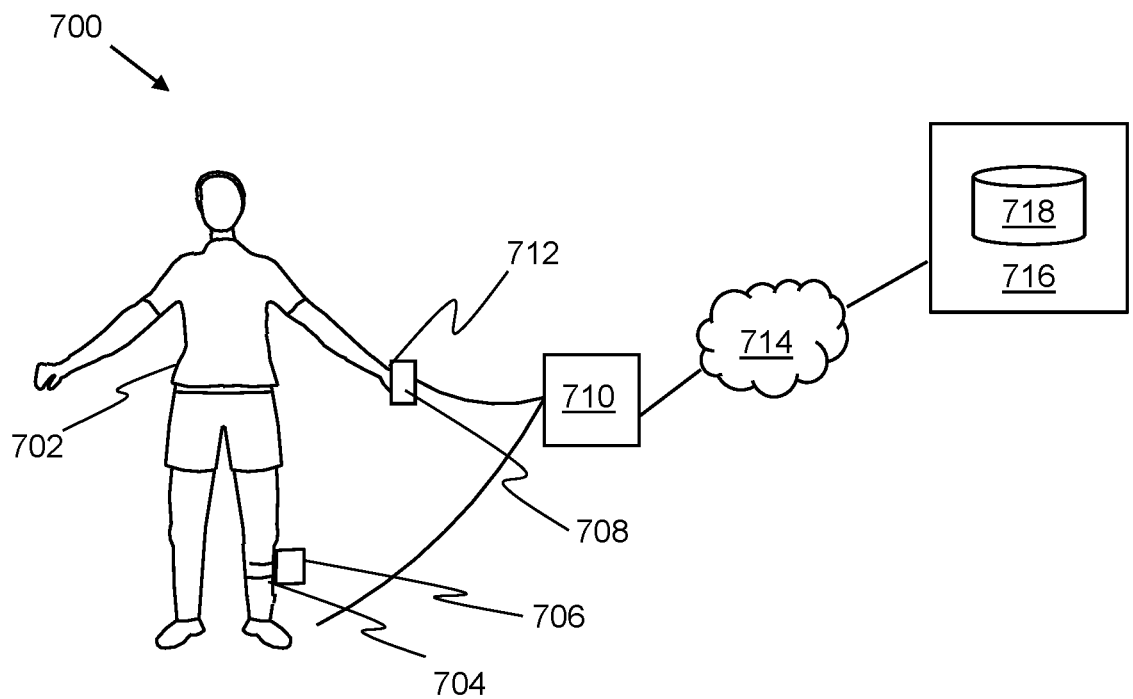
FIG. 5 is a schematic illustration of the system of FIG. 2 in a utilized state, in accordance with an embodiment of the present disclosure.

Referring to FIGS. 3-5, depicted are schematic illustrations of a system for determining a touch sensitivity threshold at a region of body of a human, in accordance with various embodiments of the present disclosure.

In FIG. 3A, the system 300 comprises a housing 302, a probe 304, a probe attachment means 312, a probe releasing means 316, a probe measurement means 320. The probe 304 comprises a tip part 306, a body part 308. The tip part 306 is connected with the body part 308. The body part 308 comprises magnetic material. The probe 304 can move inside of the housing 302 of the system 300. Initially, the probe is in position as indicated in the FIG. 3A. It is attached to said position with the probe attachment means 312. The probe attachment means 312 comprises an attachment coil 314, which is configured to be electrically controlled. The system 300 further comprises the probe releasing means 316, comprising a driver coil 318. A current is fed into the driver coil 318 in a first direction or a second direction. The probe measurement means 320 comprise a measurement coil 322. The probe 304 is configured to hit a surface 330 of region of body of the human.

In FIG. 3B, movement of the probe 304 is illustrated. The attachment coil 314 is switched off to detach the probe 304. The driver coil 318 is activated to provide magnetic force to move the probe 304 in a first direction as indicated by arrow O-A. The arrow O-A indicates the direction of movement of the probe 304. As illustrated, the probe 304 impacts the surface 330 of region of body of the human with a force. It will be appreciated that the movement of the probe 304 takes place if the induction current applied to the driver coil is sufficient to overcome force of the attachment means 312 or when the attachment coil 314 is turned OFF. During the movement of the probe 304 a current is induced in the measurement coil 322 of the measurement means 320. The current can be used to determine speed and movement of the probe 304 as well as control driving of the driver coil 318.

In FIG. 3C, the movement of the probe 304 in a second direction as indicated by arrow M-N. The arrow M-N indicates the direction of movement of the probe 304. As illustrated, the probe 304 rebounds from the surface 330 of region of body of the human in an opposite direction as indicated by arrow M-N.

Referring to FIG. 4, illustrated is schematic illustration of the system 300 when in use in accordance with an embodiment of the present disclosure. The system 300 is configured to hit the cornea of the eye 332 with a predefined impact attribute and subsequently rebound from the cornea of the eye 332.

Referring to FIG. 5, illustrated is a schematic illustration of the system 200 of FIG. 2 in a utilized state, in accordance with an embodiment of the present disclosure. As shown, the system 700 comprises a probe 706 (such as the probe 204 of FIG. 2) placed in contact with skin of a leg 704 of the human 702. The human is required to provide feedback of touch sensitivity associated with the impact of the probe 706 launched at the skin of a leg 704. The feedback is provided on the feedback means 708 (such as the feedback means 210 of FIG. 2). The feedback means 708 is held in the hand 712 of the human 702. The system 700 further comprises a server arrangement 716 (such as the server arrangement 204 of FIG. 2) communicatively coupled to the controller 710 (such as the controller 212 of FIG. 2) via a communication network 714 (such as the communication network 214 of FIG. 2). Furthermore, the server arrangement 716 comprises a database 718 (such as the database 218 of FIG. 2) operable to store the touch sensitivity thresholds for the skin of leg 704 of the human 702.

Referring to FIGS. 6-10, illustrated are graphs illustrating a change in a first value for the impact attribute to a second value for the impact attribute, in accordance with various embodiments of the present disclosure.

Figure 6:
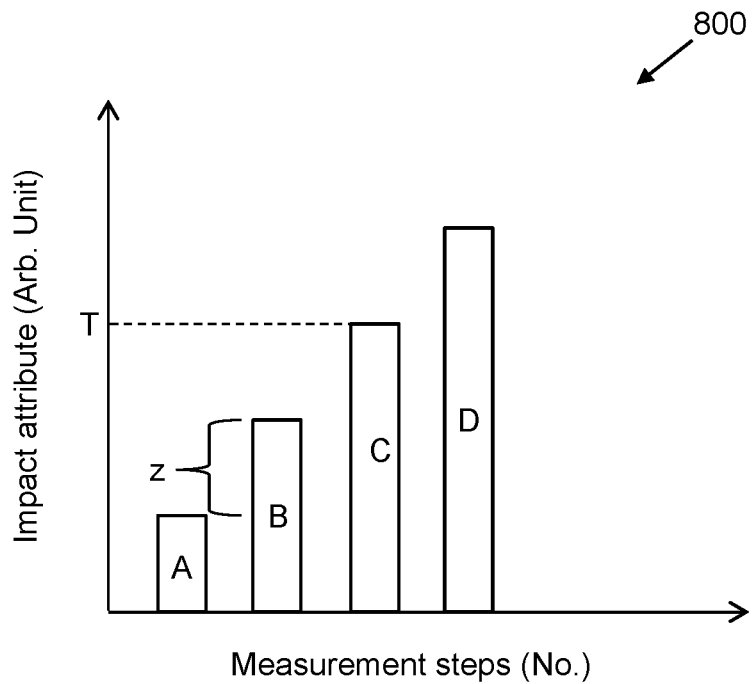
FIGS. 6-10 are graphs illustrating a change in a first value for the impact attribute to a second value for the impact attribute, in accordance with various embodiments of the present disclosure.

In FIG. 6, the graph 800 represents a relationship between changes in the first value for the impact attribute to the second value for the impact attribute, with respect to a number of measurement steps. In graph 800, a vertical axis represents the change in the first value for the impact attribute to the second value for the impact attribute, and a horizontal axis represents the number of measurement steps. As shown, the first value for the impact attribute changes to the second value for the impact attribute in discrete steps, wherein each of the steps is equal to a value 'z'. Furthermore, as shown in graph 800, bars A-D corresponds to a measurement step performed with a specific impact attribute.

More specifically, graph 800 represents a ramp-up pattern of change in the first value for the impact attribute to the second value for the impact attribute, wherein graph 800 comprises setting a first value for the impact attribute with a lower value and increasing the value of the subsequent impact attributes in equal progressive step size 'z' to impact the region of body with a probe in each measurement steps. If the feedback associated with the previous measurement step fails to report touch sensitivity at the region of body, a subsequent measurement step is evaluated to determine touch sensitivity at the region of body. The measurement steps are repeated until a feedback associated with the subsequent impact attribute is associated with touch sensitivity at the region of body of the human. Specifically, as shown in graph 800, the measurement steps with bars A and B are not associated with touch sensitivity at the region, while the measurement steps with bars C and D are associated with touch sensitivity at the region. However, the measurement step with bar C corresponding to the lowest value of impact attribute associated with touch sensitivity is selected as the touch sensitivity threshold 'T'.

Figure 7:
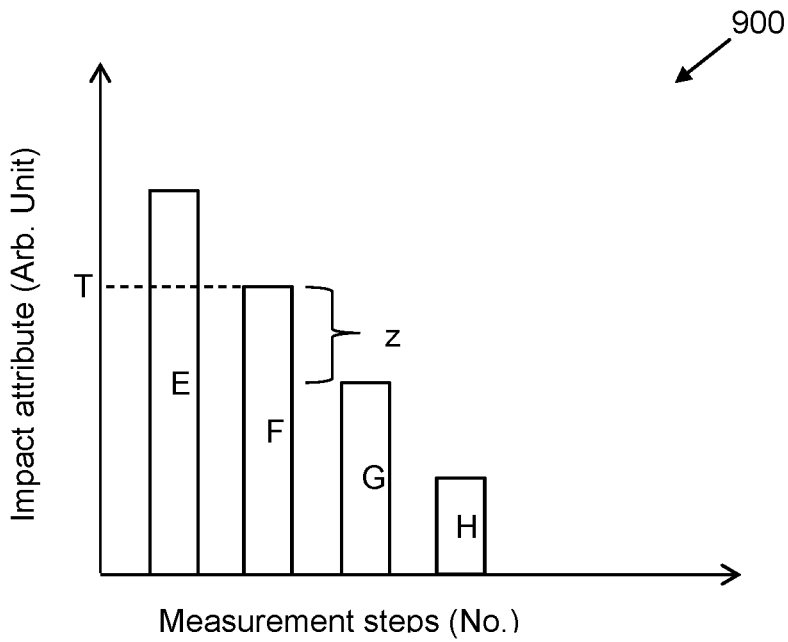

As shown in FIG. 7, the graph 900 represents a relationship between changes in the first value for the impact attribute to the second value for the impact attribute, with respect to a number of measurement steps. In graph 900, a vertical axis represents the change in the first value for the impact attribute to the second value for the impact attribute, and a horizontal axis represents the number of measurement steps. As shown, the first value for the impact attribute changes to the second value for the impact attribute in discrete steps, wherein each of the steps is equal to a value 'z'. Furthermore, as shown in graph 900, bars E-H corresponds to a measurement step performed with a specific impact attribute.

More specifically, graph 900 represents a ramp-down pattern of change in the first value for the impact attribute to the second value for the impact attribute, wherein graph 900 comprises setting a first value for the impact attribute with a higher value and decreasing the value of the subsequent impact attributes in equal regressive step size 'z' to impact the region of body with a probe in each measurement steps. If the feedback associated with the previous measurement step reports touch sensitivity at the region of body, a subsequent measurement step is evaluated to determine touch sensitivity at the region of body. The measurement steps are repeated until a feedback associated with the subsequent impact attribute is fails to report touch sensitivity at the region of body of the human. Specifically, as shown in graph 900, the measurement step with bar E and F are associated with touch sensitivity at the region, while the measurement steps with bars G and H fail to associate with touch sensitivity at the region. However, the measurement step with bar F corresponding to the lowest value of impact attribute associated with touch sensitivity is selected as the touch sensitivity threshold 'T'.

Figure 8:
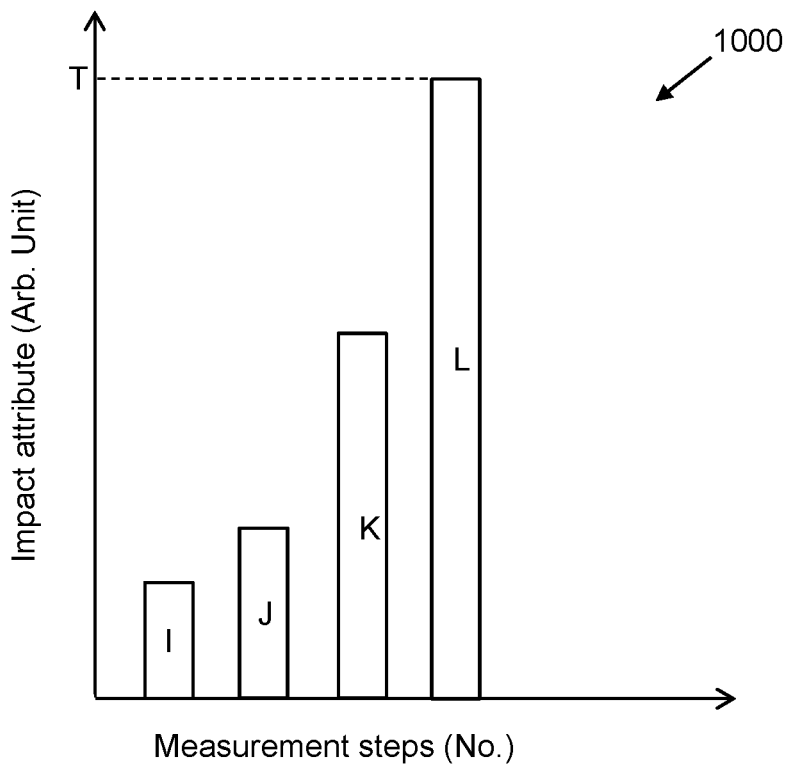

In FIG. 8, the graph 1000 represents a relationship between change in the first value for the impact attribute to the second value for the impact attribute, with respect to a number of measurement steps. In graph 1000, a vertical axis represents the change in the first value for the impact attribute to the second value for the impact attribute, and a horizontal axis represents the number of measurement steps. As shown, the first value for the impact attribute changes to the second value for the impact attribute in discrete steps, wherein each value of the steps is selected randomly. Furthermore, as shown in graph 1000, bars I-L corresponds to a measurement step performed with a specific impact attribute.

More specifically, graph 1000 represents a random pattern of change in the first value for the impact attribute to the second value for the impact attribute 1000, wherein graph 1000 comprises setting a first value for the impact attribute with a lower value and increasing the value of the subsequent impact attributes in random progressive step size to impact the region of body with a probe in each measurement steps. Specifically, as shown in graph 1000, the measurement steps with bars I, J and K are not associated with touch sensitivity at the region, while the measurement steps with bar L is associated with touch sensitivity at the region. Then, the measurement step with bar L corresponding to the lowest value of impact attribute associated with touch sensitivity is selected as the touch sensitivity threshold 'T'.

Figure 9:
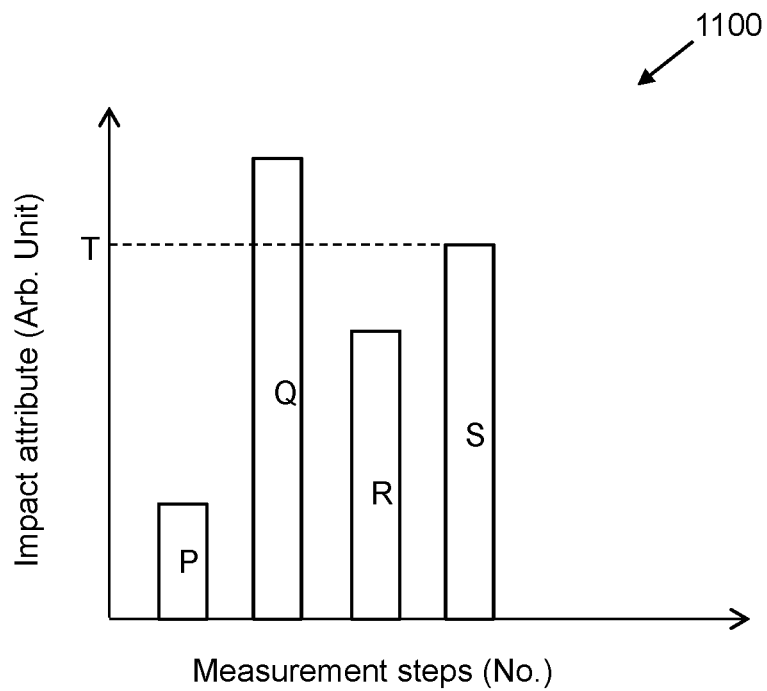

As shown in FIG. 9, the graph 1100 represents a relationship between change in the first value for the impact attribute to the second value for the impact attribute, with respect to a number of measurement steps. In graph 1100, a vertical axis represents the change in the first value for the impact attribute to the second value for the impact attribute, and a horizontal axis represents the number of measurement steps. As shown, the first value for the impact attribute changes to the second value for the impact attribute in discrete steps, wherein each value of the steps is selected randomly. Furthermore, as shown in graph 1100, bars P-S corresponds to a measurement step performed with a specific impact attribute.

More specifically, graph 1100 represents an iterative (Newton-Raphson technique) pattern of change in the first value for the impact attribute to the second value for the impact attribute, wherein graph 1100 comprises setting a first value for the impact attribute with a random lower value and changing the value of the subsequent impact attributes in random step size to impact the region of body with a probe in each measurement steps. As shown in graph 1100, the measurement steps with bars P and R are not associated with touch sensitivity at the region, while the measurement steps with bars Q and S are associated with touch sensitivity at the region. Then, the measurement step with bar S corresponding to the lowest value of impact attribute associated with touch sensitivity is selected as the touch sensitivity threshold 'T'.

Figure 10:
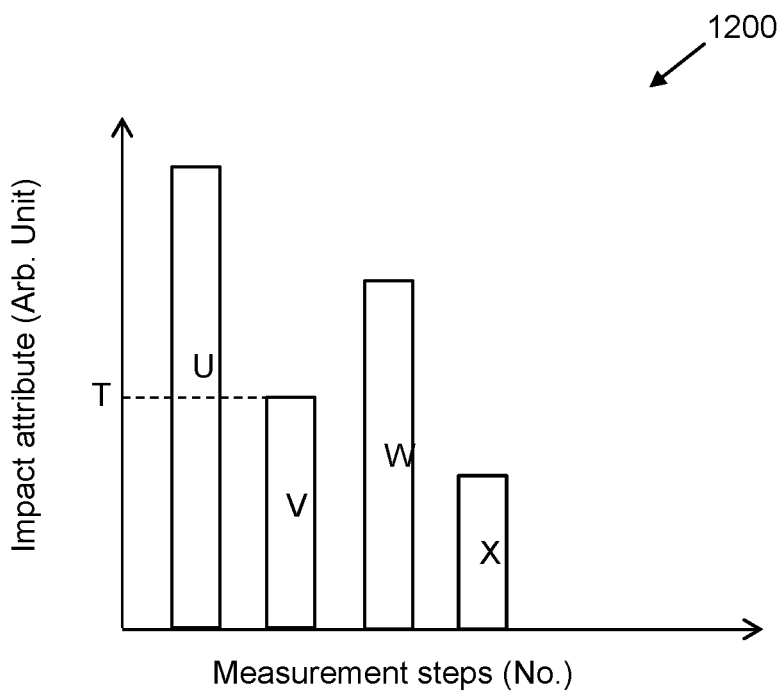

In FIG. 10, the graph 1200 represents a relationship between change in the first value for the impact attribute to the second value for the impact attribute, with respect to a number of measurement steps. In graph 1200, a vertical axis represents the change in the first value for the impact attribute to the second value for the impact attribute, and a horizontal axis represents the number of measurement steps. As shown, the first value for the impact attribute changes to the second value for the impact attribute in discrete steps, wherein each value of the steps is selected randomly. Furthermore, as shown in graph 1200, bars U-X corresponds to a measurement step performed with a specific impact attribute.

More specifically, graph 1200 represents an iterative (Newton-Raphson technique) pattern of change in the first value for the impact attribute to the second value for the impact attribute 1200, wherein graph 1200 comprises setting a first value for the impact attribute with a random higher value and changing the value of the subsequent impact attributes in random step size to impact the region of body with a probe in each measurement steps. As shown in graph 1200, the measurement steps with bars U and W are not associated with touch sensitivity at the region, while the measurement steps with bar T and V are associated with touch sensitivity at the region. Then, the measurement step with bar V corresponding to the lowest value of impact attribute associated with touch sensitivity is selected as the touch sensitivity threshold 'T'.

Figure 11:
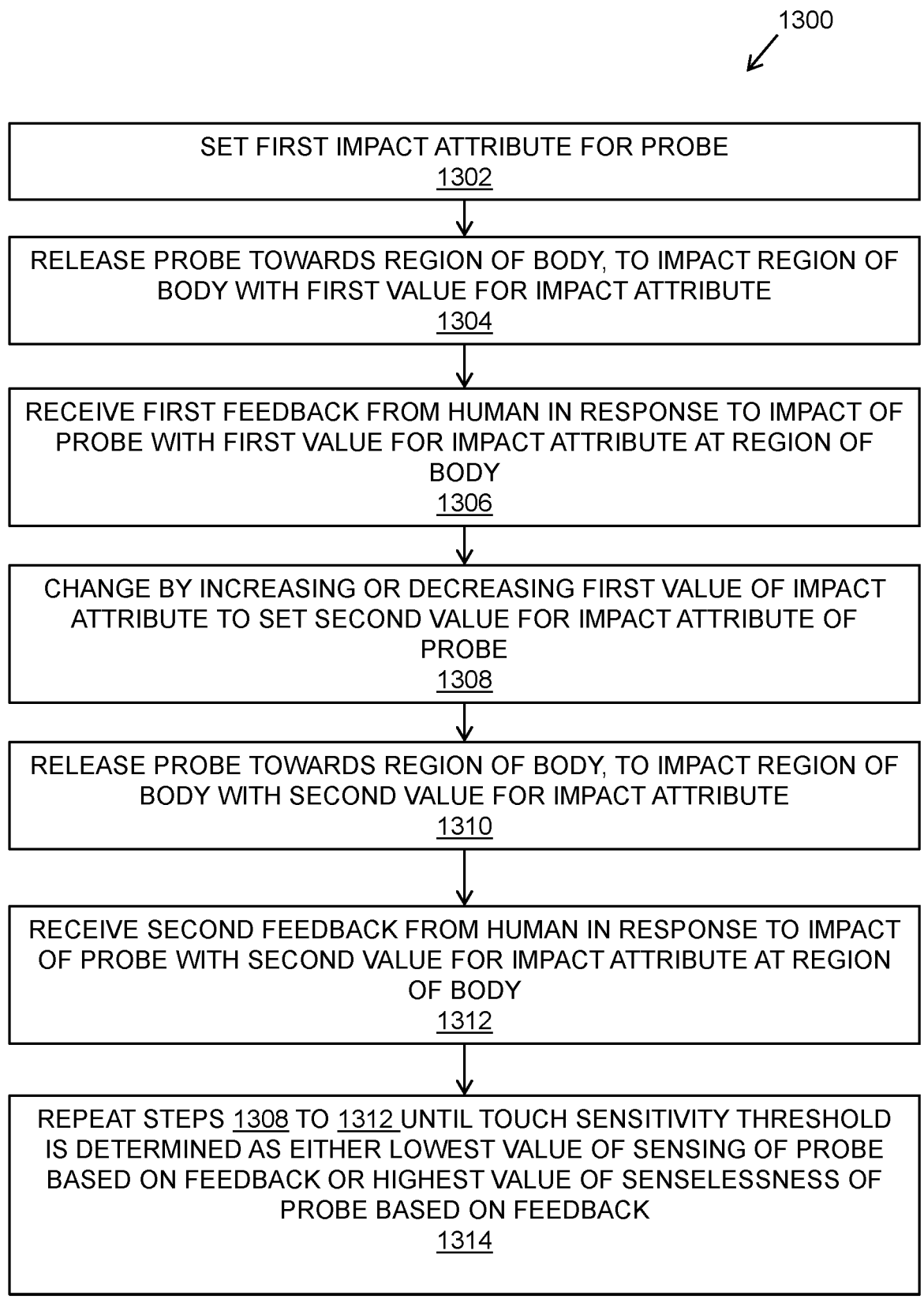
FIG. 11 is an illustration of steps of a method of determining a touch sensitivity threshold at a region of body of a human using a probe, in accordance with an embodiment of the present disclosure.

Referring to FIG. 11, there is shown an illustration of steps of a method 1300 of determining a touch sensitivity threshold at a region of body of a human using a probe, in accordance with an embodiment of the present disclosure. At step 1302, a first value for the impact attribute for the probe is set. At step 1304, the probe is released towards the region of body, to impact the region of body with the first value for the impact attribute. At step 1306, a first feedback is received from the human in response to the impact of the probe with the first value for the impact attribute at the region of body. At step 1308, the first value of the impact attribute is changed, by increasing or decreasing to set a second value for the impact attribute of the probe. At step 1310, the probe is released towards the region of body, to impact the region of body with the second value for the impact attribute. At step 1312, a second feedback is received from the human in response to the impact of the probe with the second value for the impact attribute at the region of body. At step 1314, the steps 1308 to 1312 are repeated until the touch sensitivity threshold is determined as either a lowest value of sensing of the probe based on the feedback, or a highest value of senselessness of the probe based on the feedback. The feedback corresponds to sensing of the probe or senselessness of the probe.

The steps 1302 to 1314 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for determining a touch sensitivity threshold at an eye surface, the system comprising:
   a housing comprising:
   a probe detachably arranged within the housing, wherein the probe comprises a tip part and a body part, the tip part is fabricated using a bio-compatible material, and the body part is magnetic material, and the probe is operable to impact the eye surface with a predefined impact attribute and rebound from the eye surface;
   a probe attachment means operable to retain the probe within the housing; and
   a probe release means operable to release the probe towards the eye surface, wherein the probe release means is a driver coil, wherein the driver coil is operable to produce a magnetic force to actuate the probe:
   in a first direction to release the probe from the housing; or
   in a second direction to retract the probe into the housing;
   a feedback means to receive feedback from a human after the impact of the probe with the eye surface; and
   a controller operatively coupled to the probe attachment means, the probe release means and the feedback means, wherein the controller is operable to:
   (a) set a first value for an impact attribute of the probe;
   (b) release the probe towards the eye surface, to impact the eye surface with the first value for the impact attribute;
   (c) from the human, receive a first feedback in response to perceiving touch sensation from the impact of the probe with the first value for the impact attribute at the eye surface;
   (d) change, by randomly increasing or decreasing the first value of the impact attribute to set a second value for the impact attribute of the probe;
   (e) release the probe towards the eye surface, to impact the eye surface with the second value for the impact attribute;
   (f) from the human, receive a second feedback in response to perceiving touch sensation from the impact of the probe with the second value for the impact attribute at the eye surface; and
   (g) repeat steps (d) to (f) until the touch sensitivity threshold is determined as either:
   a lowest value of sensing of the probe based on the feedback; or
   a highest value of senselessness of the probe based on the feedback,
   wherein the feedback corresponds to sensing of the probe or senselessness of the probe.

2. The system according to claim 1, wherein the controller is operable to:
   increase the value of the impact attribute until the feedback corresponds to sensing at the eye surface;
   decrease the value of the impact attribute until the feedback corresponds to senselessness at the eye surface; or
   randomly vary the value of the impact attribute until the feedback corresponds to one of sensing at the eye surface or senselessness at the eye surface.

3. The system according to claim 1, wherein the housing has a tubular form-factor.

4. The system according to claim 1, wherein the probe attachment means is an attachment coil.

5. The system according to claim 1, further comprising a probe measurement means, wherein the probe measurement means comprises a measurement coil being operable to measure the current resulting from the movement of the probe after launch and rebound of the probe respectively, and wherein the probe measurement means is operable to determine the impact attribute of the probe associated with impact of the probe with the eye surface.

6. The system according to claim 1, wherein the impact attribute comprises at least one of: speed, acceleration, kinetic energy, kinetic energy per unit area of impact, momentum, momentum per unit area of impact, pressure induced by the impact, duration of impact.

7. The system according to claim 1, wherein the probe is associated with at least one of: a predetermined weight, or a predefined form-factor.

8. The system according to claim 1, further comprising a separator part operatively coupled to the housing wherein the separator part maintains a predefined separation between the housing and the eye surface of the human.

9. The system according to claim 1, further comprising a server arrangement communicatively coupled to the controller via a communication network, wherein the server arrangement comprises a database operable to store the touch sensitivity thresholds for a plurality of humans.

10. The system according to claim 9, wherein the server arrangement is operable to:
   determine a reference touch sensitivity threshold using the touch sensitivity thresholds of the plurality of humans; and
   store the reference touch sensitivity threshold within the database, and optionally the controller is further operable to:
      receive the reference touch sensitivity threshold from the server arrangement;
      determine a difference between the touch sensitivity threshold of the human and the reference touch sensitivity threshold; and
      correlate the difference with a potential medical condition for the human.

11. The system according to claim 1, wherein the feedback means is implemented as an input device, wherein the input device comprises a user interface or one or more buttons for tactile feedback, wherein, the input device comprises at least one of: the user interface, a keypad, or an audio receiver.

\* \* \* \* \*